US010755452B2

(12) United States Patent
Wang et al.

(10) Patent No.: US 10,755,452 B2
(45) Date of Patent: Aug. 25, 2020

(54) CALIBRATING TIME IN PET DEVICE

(71) Applicant: Shanghai Neusoft Medical Technology Co., Ltd., Shanghai (CN)

(72) Inventors: Xi Wang, Shenyang (CN); Jian Zhao, Shenyang (CN); Guocheng Wu, Shenyang (CN); Baowei Xu, Shenyang (CN); Guodong Liang, Shenyang (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 56 days.

(21) Appl. No.: 16/019,107

(22) Filed: Jun. 26, 2018

(65) Prior Publication Data
US 2019/0012812 A1    Jan. 10, 2019

(30) Foreign Application Priority Data

Jul. 10, 2017  (CN) .......................... 2017 1 0556109

(51) Int. Cl.
A61B 6/03      (2006.01)
G01T 1/29      (2006.01)
(Continued)

(52) U.S. Cl.
CPC ............ *G06T 11/005* (2013.01); *A61B 6/037* (2013.01); *A61B 6/4241* (2013.01); *A61B 6/585* (2013.01);
(Continued)

(58) Field of Classification Search
None
See application file for complete search history.

(56) References Cited

U.S. PATENT DOCUMENTS 8,796,637 B1    8/2014 Burr et al.
2010/0078569 A1    4/2010 Jarron et al.
(Continued)

FOREIGN PATENT DOCUMENTS

CN    103488247 A    1/2014
CN    103961126 A    8/2014
(Continued)

OTHER PUBLICATIONS

State Intellectual Property Office of the People's Republic of China, Office Action and Search Report Issued in Application No. 201710493862.6, dated Oct. 29, 2018, 4 pages, (Submitted with Machine Translation).

(Continued)

*Primary Examiner* — Idowu O Osifade
(74) *Attorney, Agent, or Firm* — Fish & Richardson P.C.

(57) ABSTRACT

A method of calibrating time in a Positron Emission Tomography (PET) device includes obtaining original time information and energy information of a first pulse signal collected by a detecting module during a scanning process of the PET device. A detector of the PET device includes a plurality of detecting modules. The original time information of the first pulse signal includes a moment at which an amplitude of the first pulse signal begins to be greater than a threshold. The method includes determining a pulse time calibration amount corresponding to the energy information of the first pulse signal according to stored information indicative of a correspondence between the pulse time calibration amount and the energy information of each detecting module. The method includes generating calibrated time information of the first pulse signal by calibrating the original time information with the pulse time calibration amount; and reconstructing a PET image based on the generated calibrated time information.

20 Claims, 4 Drawing Sheets

(51) Int. Cl.
*G06T 11/00* (2006.01)
*A61B 6/00* (2006.01)

(52) U.S. Cl.
CPC .......... *G01T 1/2985* (2013.01); *A61B 6/4266* (2013.01); *G06T 2210/41* (2013.01); *G06T 2211/424* (2013.01)

(56) References Cited

U.S. PATENT DOCUMENTS

| | | | |
|---|---|---|---|
| 2011/0210255 A1 | 9/2011 | Kim et al. | |
| 2015/0285922 A1 | 10/2015 | Mintzer et al. | |
| 2015/0297168 A1* | 10/2015 | Panin | A61B 6/585 600/427 |
| 2015/0363948 A1* | 12/2015 | Leahy | A61B 6/037 600/425 |
| 2016/0299240 A1 | 10/2016 | Cho et al. | |

FOREIGN PATENT DOCUMENTS

| | | |
|---|---|---|
| CN | 103969675 A | 8/2014 |
| CN | 104644204 A | 5/2015 |
| CN | 105030263 A | 11/2015 |
| CN | 105193442 A | 12/2015 |
| CN | 105204060 A | 12/2015 |
| CN | 105737853 A | 7/2016 |
| CN | 106716179 A | 5/2017 |

OTHER PUBLICATIONS

European Patent Office, Extended European Search Report Issued in Application No. 18182480.6, dated Oct. 22, 2018, Germany, 10 pages.

Schug David et al:"Crystal Delay and Time Walk Correction Methods for Coincidence Resolving Time Improvements of a Digtal-Silicon-Photomultiplier-Based PET/MRI Insert". IEEE Transactions on Radiation and Plasma Medical Sciences, IEEE. vol. 1,No. 2, Mar. 1, 2017(Mar. 1, 2017), pp. 178-190, XP011643930, ISSN:2469-7311, DOI: 10.1109/TNS.2017.2654920 [retrieved on Mar. 24, 2017] p. 179-p. 189.

State Intellectual Property Office of the People's Republic of China, Office Action and Search Report Issued in Application No. 2017105561097, dated Mar. 19, 2020, 33 pages, (Submitted with Machine Translation).

* cited by examiner

CALIBRATING TIME IN PET DEVICE

CROSS REFERENCE TO RELATED APPLICATIONS

This application claims priority to Chinese Patent Application No. 201710556109.7, filed on Jul. 10, 2017, the entire content of which is incorporated herein by reference.

BACKGROUND

In a Positron Emission Tomography (PET) device, a tracer containing radionuclides is injected in a subject and positrons are generated due to the decay of the tracer. A positron is annihilated with a negative electron within the subject, resulting in the generation of a photon pair containing two photons. The two photons are emitted in opposite directions. A PET image is reconstructed by a series of processes after an annular detector of the PET device detects the photon pair.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

This disclosure relates to an approach to calibrating time in a PET device. When a PET detector detects a photon, the detector may be configured to convert the photon into a pulse voltage signal or a pulse current signal. The corresponding pulse waveform exhibits a characteristic of linear rising and exponential attenuation over time. By setting a comparator with a threshold, a moment at which an amplitude of the pulse signal begins to be greater than the threshold may be determined as time information of the pulse signal (may also be referred to as time information of the photon), i.e. time information at which the photon is detected by the detector. Calibration of time information can help to improve the accuracy of the detected time information of the pulse signal, which in turn can improve the quality of reconstructed PET images generated based on the detected information. Higher quality PET images can have advantages for improved diagnosis and treatment of patients.

In an aspect, a method of calibrating time in a Positron Emission Tomography (PET) device includes obtaining original time information and energy information of a first pulse signal collected by a detecting module during a scanning process of the PET device. A detector of the PET device includes a plurality of detecting modules. The original time information of the first pulse signal includes a moment at which an amplitude of the first pulse signal begins to be greater than a threshold. The method includes determining a pulse time calibration amount corresponding to the energy information of the first pulse signal according to stored information indicative of a correspondence between the pulse time calibration amount and the energy information of each detecting module. The method includes generating calibrated time information of the first pulse signal by calibrating the original time information with the pulse time calibration amount; and reconstructing a PET image based on the generated calibrated time information.

Embodiments can include one or more of the following features.

The method includes establishing a correspondence between the pulse time calibration amount and the energy information of each of the detecting modules during a system calibration process of the PET device; and storing the correspondence between the pulse time calibration amount and the energy information of each of the detecting modules.

The correspondence between the pulse time calibration amount and the energy information of a given detecting module is characterized by any one of following function relationships: a linear function, an exponential function, a power function and a polynomial function. Each of the function relationships includes a function model and function parameters corresponding to the function model.

The correspondence between the pulse time calibration amount and the energy information of each of the detecting modules in the detector is characterized by the same function model.

Establishing the correspondence between the pulse time calibration amount and the energy information of a given detecting module includes determining a function model; obtaining data of second pulse signals collected by the detecting module during the system calibration process; and determining values of one or more function parameters corresponding to the function model by calculating the data of the second pulse signals.

Obtaining the data of the second pulse signals collected by the detecting module during the system calibration process includes obtaining information of N second pulse signals by sampling output of the detecting module during the system calibration process with a sampling module. N is an integer greater than 1. The information of each of the N second pulse signals includes a combination of amplitude information and time information. The sampling module includes a data acquisition card or an oscilloscope. Obtaining the data of the second pulse signals includes obtaining energy information of each of the N second pulse signals by performing a numerical integration operation for the amplitude information of the second pulse signal; and obtaining a pulse time calibration amount of each of the N second pulse signals by calculating a difference between a start moment and an over-threshold moment of the second pulse signal. The over-threshold moment of the second pulse signal indicates a moment at which an amplitude of the second pulse signal begins to be greater than the threshold.

Calculating the data of the second pulse signals includes calculating the data of the second pulse signals by a fitting algorithm.

Calculating the data of the second pulse signals includes calculating the data of the second pulse signals by an iterative algorithm. Calculating the data of the second pulse signals by the iterative algorithm includes taking the one or more function parameters corresponding to the function model as iteration variables; determining new time information of each of the second pulse signals based on a value of the respective function parameters, energy information of the second pulse signal and time information of the second pulse signal obtained in a prior iteration; and when a system time resolution obtained based on the new time information of each of the second pulse signals reaches an optimum, taking values of the iteration variables corresponding to the optimum as the values of the one or more function parameters when the function model is applied to the detecting module.

Storing the correspondence between pulse time calibration amount and energy information of the respective detecting modules includes one of storing a function model and one or more function parameters corresponding to the function model; and storing a pulse time calibration amount-energy information table for each of the detecting modules, wherein record energy information and a pulse time calibration amount generated by the correspondence are recorded in an entry of the table.

In an aspect, a PET system includes a PET device; one or more processors; and a non-transitory machine readable storage medium. The one or more processors are configured to invoke machine executable instructions stored in the non-transitory machine readable storage medium to obtain original time information and energy information of a first pulse signal collected by a detecting module during a scanning process of the PET device. A detector of the PET device includes a plurality of detecting modules. The original time information of the first pulse signal includes a moment at which an amplitude of the first pulse signal begins to be greater than a threshold. The one or more processors are configured to invoke machine executable instructions to determine a pulse time calibration amount corresponding to the energy information of the first pulse signal according to stored information indicative of a correspondence between the pulse time calibration amount and the energy information of each detecting module; generate calibrated time information of the first pulse signal by calibrating the original time information with the pulse time calibration amount; and reconstruct a PET image based on the generated calibrated time information.

Embodiments can include one or more of the following features.

The one or more processors are configured to invoke the machine executable instructions to establish a correspondence between the pulse time calibration amount and the energy information of each of the detecting modules during a system calibration process of the PET device; and store the correspondence between the pulse time calibration amount and the energy information of each of the detecting modules.

The correspondence between the pulse time calibration amount and the energy information of a given detecting module is characterized by any one of following function relationships: a linear function, an exponential function, a power function and a polynomial function. Each of the function relationships includes a function model and function parameters corresponding to the function model.

The correspondence between the pulse time calibration amount and the energy information of each of the detecting modules in the detector is characterized by the same function model.

Establishing the correspondence between the pulse time calibration amount and the energy information of a given detecting module includes determining a function model; obtaining data of second pulse signals collected by the detecting module during the system calibration process; and determining values of one or more function parameters corresponding to the function model by calculating the data of the second pulse signals.

Obtaining the data of the second pulse signals collected by the detecting module during the system calibration process includes obtaining information of N second pulse signals by sampling output of the detecting module during the system calibration process with a sampling module. N is an integer greater than 1. The information of each of the N second pulse signals includes a combination of amplitude information and time information. The sampling module includes a data acquisition card or an oscilloscope. Obtaining the data of the second pulse signals includes obtaining energy information of each of the N second pulse signals by performing a numerical integration operation for the amplitude information of the second pulse signal; and obtaining a pulse time calibration amount of each of the N second pulse signals by calculating a difference between a start moment and an over-threshold moment of the second pulse signal. The over-threshold moment of the second pulse signal indicates a moment at which an amplitude of the second pulse signal begins to be greater than the threshold.

Calculating the data of the second pulse signals includes calculating the data of the second pulse signals by a fitting algorithm.

Calculating the data of the second pulse signals includes calculating the data of the second pulse signals by an iterative algorithm. Calculating the data of the second pulse signals by the iterative algorithm includes take the one or more function parameters corresponding to the function model as iteration variables; determine new time information of each of the second pulse signals based on a value of the respective function parameters, energy information of the second pulse signal and time information of the second pulse signal obtained in a prior iteration; and when a system time resolution obtained based on the new time information of each of the second pulse signals reaches an optimum, take values of the iteration variables corresponding to the optimum as the values of the one or more function parameters when the function model is applied to the detecting module.

Storing the correspondence between pulse time calibration amount and energy information of the respective detecting modules includes storing a function model and one or more function parameters corresponding to the function model; and storing a pulse time calibration amount-energy information table for each of the detecting modules, wherein energy information and a pulse time calibration amount generated by the correspondence are recorded in an entry of the table.

DETAILED DESCRIPTION

We describe here an approach to calibrating time information in a PET system. The accuracy of time information of a pulse signal detected in a PET system can affect the quality of the PET image reconstructed from that pulse signal. By calibrating original time information of a pulse signal with energy information of the pulse signal, the accuracy of the time information can be improved, which can result in improved image reconstruction. Higher quality image reconstructions can have implications for improved diagnostic and treatment outcomes.

Figure 1A:
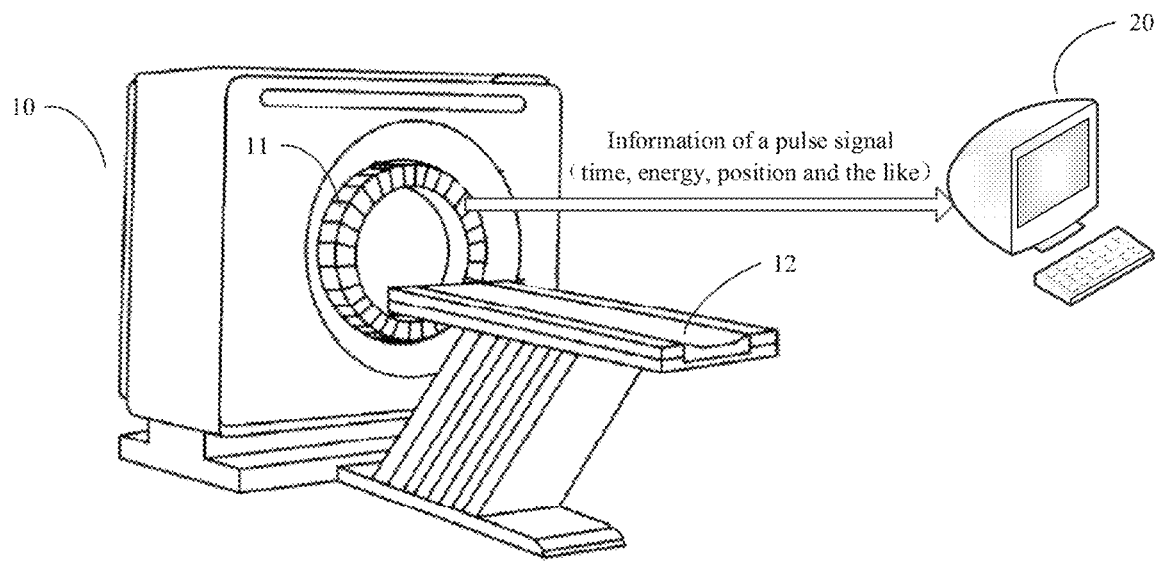
FIG. 1A is a schematic diagram of a PET system.

FIG. 1A is a schematic diagram of an example PET system. The PET system includes a PET device 10 and a console device 20. The PET device 10 includes a detector 11 and a scanning bed 12. The detector 11 may be an annular detector as shown in FIG. 1A. The annular detector 1 includes a plurality of detecting modules. Each of the plurality of detecting modules includes sequentially connected scintillation crystals (not shown in FIG. 1A), a photoelectric converter (not shown in FIG. 1A) and a processing circuit (not shown in FIG. 1A). In an example, the processing circuit includes a data acquisition (DAQ) system circuit. The DAQ system circuit includes sub-circuits that can implement different functions, such as a front-end data acquisition circuit. The scanning bed 12 can drive a subject into the detector 11 for scanning.

When using the PET system shown in FIG. 1A, a tracer containing radionuclides is injected into the subject before scanning. During the scanning process, positrons may be generated due to the decay of radionuclides, and a positron is annihilated with a negative electron within the subject, thereby generating a pair of back-to-back gamma photons. The gamma photon pairs can be detected by scintillation crystals in a pair of detecting modules in the detector 11. The scintillation crystals convert the detected gamma photons into photon signals and transmit the photon signals to the photoelectric converter. The photoelectric converter converts the photon signals into electrical signals and transmits the electrical signals to a processing circuit. The processing circuit determines and outputs information of the pulse signal corresponding to the detected photon based on the electrical signal, such as time information, energy information, position information, or other types of information.

Detection of a gamma photon by the detecting module is referred to as an event. Two events from the same annihilation event are referred to as a coincidence event. Information about a coincidence event may be used to reconstruct a PET image. In the context of the PET system of FIG. 1A, the output of each of the detecting modules of the detector 11 may be connected to a coincidence processing circuit of the detector 11. The coincidence processing circuit may determine the occurrence of a coincidence event according to information of the pulse signal and transmit information of a pair of pulse signals corresponding to the coincidence event to the console device 20 for image reconstruction.

In determining the occurrence of a coincidence event and reconstructing images based on coincidence events, time information and energy information of pulse signals acquired by a detecting module are relevant. Taking time of flight (TOF) as an example, the PET system may estimate an approximate position at which a positron is annihilated with a negative electron based on the TOF of a gamma photon pair detected by a pair of detecting modules. The approximate position may be used to reconstruct a PET image. Given the role of TOF in image reconstruction, accuracy of time information of a pulse signal can affect the quality of the reconstructed PET image.

The processing circuit in each of the detecting modules of the detector 11 may include a comparator having an associated threshold. The comparator is configured to identify a moment at which an amplitude of a pulse signal begins to be greater than the threshold (sometimes referred to as an over-threshold moment) as time information of the pulse signal. Since the threshold is a fixed value and the difference between pulse waveforms corresponding to photons having different energies is not taken into consideration by the single threshold of the comparator, there is a timewalk between time information of photons identified by the comparator. This is because, even if photons from positron annihilation events all are gamma photons, the energy of the photons may be different, causing a difference in the time information of the corresponding pulse signals. This timewalk can affect the quality of the PET image reconstructed based on the time information of the pulse signals.

Figure 1B:
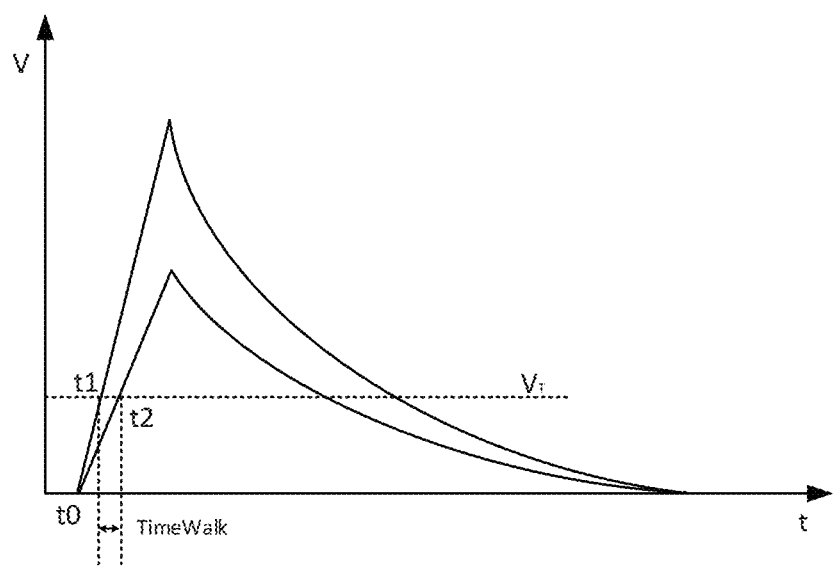
FIG. 1B is a schematic diagram of time-voltage pulse waveforms of two photons.

FIG. 1B is a plot of example time (t)-voltage (V) pulse waveforms of two photons. $V_T$ represents a threshold of the comparator. The start moments of pulse waveforms corresponding to both photons are t0, but the identified time information t1 and t2 of these two photons based on the threshold $V_T$ has a timewalk. Due to the different energy of the two photons, the over-threshold moments of the pulse signals corresponding to the photons produces a shift, thereby resulting in the timewalk between time information of the photons of different energies.

We describe here an approach to establishing a correspondence between pulse time calibration amount and energy information for each of the detecting modules of the PET system based on a characteristic of the detectors of the PET device. During scanning of the PET device, when obtaining original time information and energy information of a pulse signal collected by a detecting module, a pulse time calibration amount of the pulse signal may be obtained based on the energy information and the established correspondence. The original time information of the pulse signal may be calibrated with the time calibration amount of the pulse signal to enhance the accuracy of the time information of the pulse signal, thereby improving the quality of the reconstructed PET image.

Figure 2A:
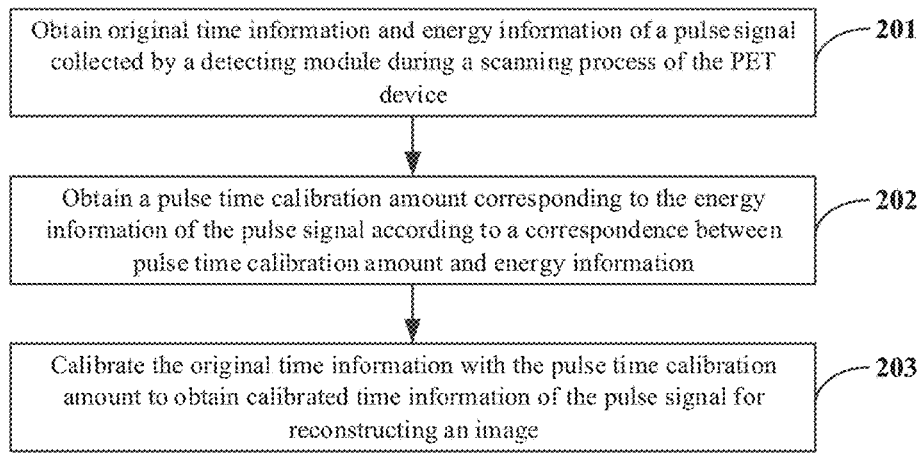
FIG. 2A is a flow chart of a method of calibrating time in a PET device.

FIG. 2A is a flow chart of an example method of calibrating time in the PET device, e.g., the PET system of FIG. 1A. The time calibration processes described here may be performed on the PET device or on the console device. The process of calibrating time includes elements 201-203.

Original time information and energy information of a pulse signal collected by a detecting module are obtained during a scanning process of the PET device (201). When the PET device itself carries out the calibration process, the processing circuit of the detecting module in the detector directly collects the original time information and energy information of the pulse signal. When the console device carries out the calibration process, the detecting module in the detector may transmit the original time information and energy information of the pulse signal collected by the processing circuit to the console device.

With reference to FIG. 1A, a scintillation crystal in each of the detecting modules detects a gamma photon, then converts the gamma photon into a photon signal and transmits the photon signal to the photoelectric converter. The photoelectric converter converts the photon signal into an electric signal and transmits the electric signal to the processing circuit. The processing circuit collects time information and energy information of a pulse signal corresponding to the detected gamma photon based on the electric signal. The time information before calibration, such as the time information of the pulse signal collected by the processing circuit, is sometimes referred to as the original time information and the time information after calibration is sometimes referred to as the calibrated time information.

A pulse time calibration amount corresponding to the energy information of the pulse signal is obtained according to a correspondence between pulse time calibration amount and energy information (202).

During a system calibration process of the PET device, by analyzing a scatter diagram between pulse time calibration amounts and energy information of pulse signals collected by different detecting modules in the detector, pulse time calibration amounts can be correlated to energy information. The correlation can be based on characteristics of the detector. A pulse time calibration amount of a pulse signal is a difference between a start moment of the pulse signal and an over-threshold moment of the pulse signal.

Figure 2B:
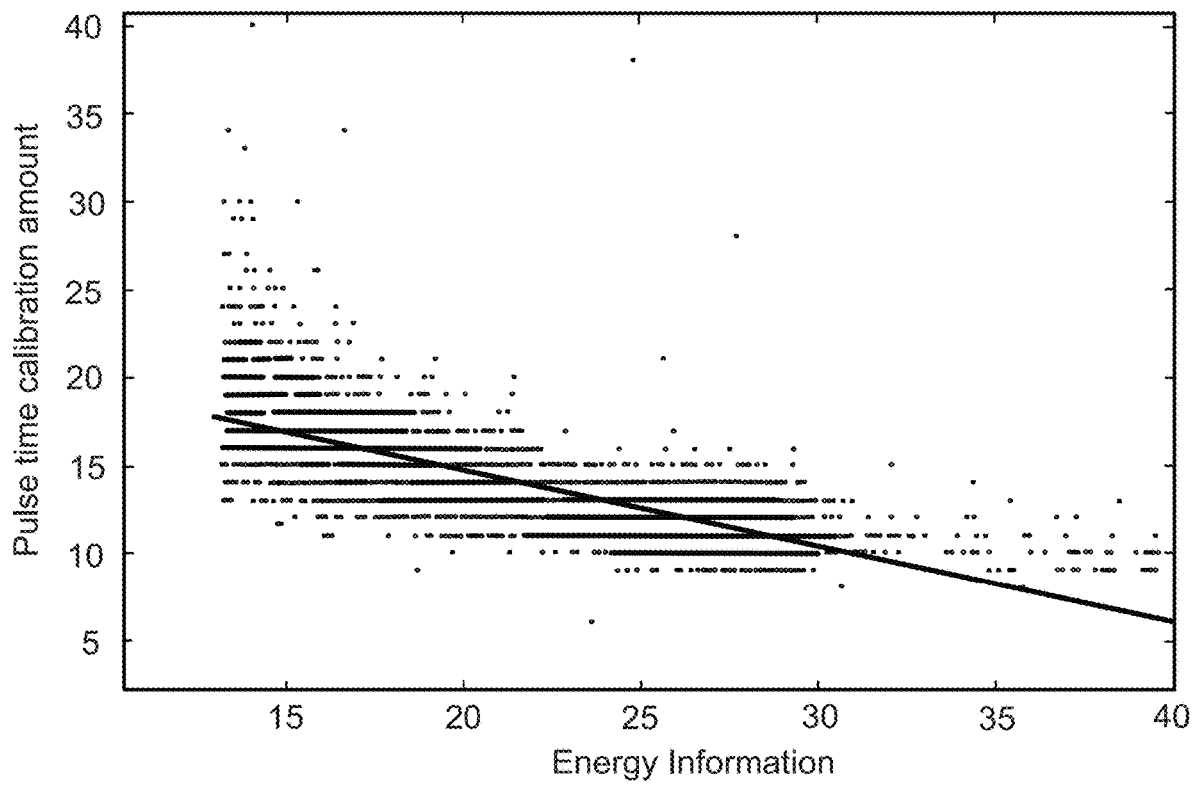
FIG. 2B is a scatter diagram between pulse time calibration amount and energy information of a detection module of a detector.

The correspondence (e.g., correlation) between pulse time calibration amounts and energy information may be characterized by different function relationships, such as linear function, exponential function, power function, polynomial function, or other types of functions. The above-described correlation of respective detecting modules in the same detector may also be characterized by a function relationship. FIG. 2B is a scatter diagram of an example of correlation between pulse time calibration amount and energy information of a detection module of a detector ac. In the example of FIG. 2B, pulse time calibration amounts and energy information are correlated by a linear function.

The function relationship between pulse time calibration amount and energy information is pre-analyzed for each of the detecting modules of the detector as part of the system calibration process, thereby pre-configuring a function model corresponding to the detector. In particular, when the PET device performs the system calibration process, the correspondence (e.g., correlation) between pulse time calibration amount and energy information of each of the detecting modules is pre-established, e.g., by the console device. The correspondence may be characterized by a function relationship, such as a linear function, exponential function, power function, or another type of function. Each of the function relationships may include a function model and one or more function parameters for the function model. Taking a linear function as an example, the function model may be y=ax+b, where a and b represent function parameters for the function model.

In an example, to establish the correspondence (e.g., correlation) between pulse time calibration amount and energy information for each of the detecting modules, the console device may acquire data of multiple pulse signals collected by each of the detecting modules. Based on the acquired data, the console device may generate function parameters corresponding to the function model of each of the detecting modules by processing the data of the pulse signals using a fitting algorithm or an iterative algorithm, based on the function model for the detector of the PET device.

In an example, the correspondence (e.g., correlation) between pulse time calibration amount and energy information is a linear function. Representing the pulse time calibration amount by deltaT and the energy information by E, the correspondence correlation between pulse time calibration amount and energy information may be represented by the formula 1 as follows:

$$deltaT = a \times E + b \quad (1).$$

The following describes how to calculate the linear function parameters a and b by a fitting algorithm and an iterative algorithm, respectively, for any of the detecting modules of the detector.

In some examples, the linear function parameters a and b are calculated by a fitting algorithm. In a fitting algorithm approach, information of a preset number of N pulse signals is obtained by sampling the output of the detecting module during the system calibration process with a sampling module. N is an integer greater than 1. When the N pulse signals are voltage signals, the information of each of the N pulse signals may include a combination of voltage information and time information. An example of the combination can be the pulse waveform as shown in FIG. 1B. The energy information E of the pulse signal may be obtained by performing a numerical integration operation for the voltage information of the pulse signal. The pulse time calibration amount of the pulse signal may be obtained by calculating a difference between a start moment t0 of the pulse signal and an over-threshold moment t1 of the pulse signal. When the pulse time calibration amount and the energy information of each of the N pulse signals are obtained, the linear function parameters a and b of the detecting module may be obtained by performing a fitting algorithm for the pulse time calibration amount and the energy information of each of the N pulse signals.

The number N of pulse signals may be adjusted as desired. The fitting algorithm may be any of a variety of fitting algorithms known to those skilled in the art, such as a least square method or another type of fitting algorithm. The sampling module may be integrated on the console device or may be provided independently of the console device. For example, the sampling module can be a data acquisition card, an oscilloscope, or another device capable of carrying out the function of the sampling module.

In some examples, the linear function parameters a and b are calculated by an iterative algorithm. In the iterative algorithm approach, the console device may acquire data of N pulse signals collected by the detecting module. N is an integer greater than 1. The data of each pulse signal i (i is an integer from 1 to N) includes time information Ti and energy information Ei of the pulse signal i. In some examples, the iterative operation is performed based on a linear function and a system time resolution is calculated based on new time information obtained by each iteration. In this way, during the iterative process, by taking the parameters a and b as iteration variables and the system time resolution as a target variable, an iteration formula (2) may be constructed as follows:

$$Ti' = Ti + a \times Ei + b \quad (2).$$

Ti represents time information of the pulse signal i; and Ti' represents new time information obtained by each iteration. The system time resolution represents a full width at a top half of a Gaussian distribution curve. The Gaussian distribution curve represents a distribution of a difference between time information of a first photon detected by a first detecting module and time information of a second photon detected by a second detecting module, where the first photon and the second photon are from a same positron annihilation event. During each iteration, the new time information generated by each iteration is applied to determine the system time resolution.

At the start of the iteration (Ti'=Ti.), 0 is assigned to the parameter a, and 0 is assigned to the parameter b. During each subsequent iteration, new values are assigned to the parameter a and the parameter b, and a new Ti' can be obtained by formula (2). A new system time resolution can be determined by the new Ti'. The above iteration is repeated until the system time resolution reaches an optimum value. The parameters a and b when the optimum value is obtained are identified as the linear function parameters. In some examples, the optimum value of the system time resolution may be pre-set empirically.

When the correspondence between pulse time calibration amount and energy information is established for the detecting module by the console device, the correspondence may be stored in a storage medium of the console device.

In some examples, the function model and the function parameters for the detecting modules are stored. Because the each of the detecting modules of the same detector adopts the same function model, the pre-configured function model and the function parameters for the respective detecting modules may be stored. To distinguish the function parameters for different detecting modules, the detecting modules may be numbered and each set of function parameters may be stored in accordance with the corresponding number. Under this storage method, a time calibration amount of a pulse signal may be calculated in real time based on the function model and the corresponding function parameters. Taking the linear function as an example, the function model deltaT=a×E+b and the function parameters a, b for the each detecting modules may be stored in the console device.

In some examples, a pulse time calibration amount-energy information table for the respective modules is stored. An entry of the table is used to record energy information and a pulse time calibration amount generated by the correspondence. Because the function model and corresponding function parameters for each of the detecting modules are known for each of the detecting modules, a value of energy information can be pre-determined based on a range of the energy information. Then the corresponding pulse time calibration amount can be determined with the correspondence based on the value of the energy information. The pulse time calibration amount-energy information table for each detecting module can then be generated. To distinguish the tables for different detecting modules, the detecting modules may be numbered and each table may be stored in accordance with the corresponding number. Under this storage method, a time calibration amount of a pulse signal may be determined in real time with the table.

Referring again to FIG. 2A, when the console device performs the process for correlating pulse time calibration amount and energy information (202), when receiving the original time information and energy information transmitted by the detecting module, the console device may read the correspondence of the detecting module from the storage medium and obtain the pulse time calibration amount corresponding to energy information according to the correspondence.

When the PET device performs the process for correlating pulse time calibration amount and energy information, the console device may configure the correspondence of each of the detecting modules to the corresponding detecting module before the PET device performs a scanning process, e.g., to a logic device in the processing circuit of the detecting module. The logic device may include a Field Programmable Gate Array (FPGA) device, Digital Signal Processing (DSP) device, or another type of logic device. The correspondences are stored in the corresponding detecting module. When the original time information and energy information of the pulse signal is collected by the detecting module of the PET device, the pulse time calibration amount corresponding to the energy information is obtained according to the stored correspondence.

The original time information is calibrated with the pulse time calibration amount to obtain calibrated time information of the pulse signal for reconstructing an image (203). The process for obtaining calibrated time information of the pulse signal can be carried out by the console device or the PET device. After obtaining the pulse time calibration amount, the original time information may be calibrated with the following formula (3):

$$Ti' = Ti + \text{delta}(Ei) \qquad (3).$$

Ti represents the original time information of the pulse signal i and Ti' represents the calibrated time information of the pulse signal i.

During the scanning process of the PET device, after obtaining the original time information and the energy information of the pulse signal collected by the detecting module, a pulse time calibration amount may be obtained according to the energy information and the established correspondence. Calibrated time information is generated by calibrating the original time information with the pulse time calibration amount to reconstruct a PET image. This approach enables an improvement in the accuracy of time information of the pulse signal, thereby improving the quality of the reconstructed PET image.

Figure 3:
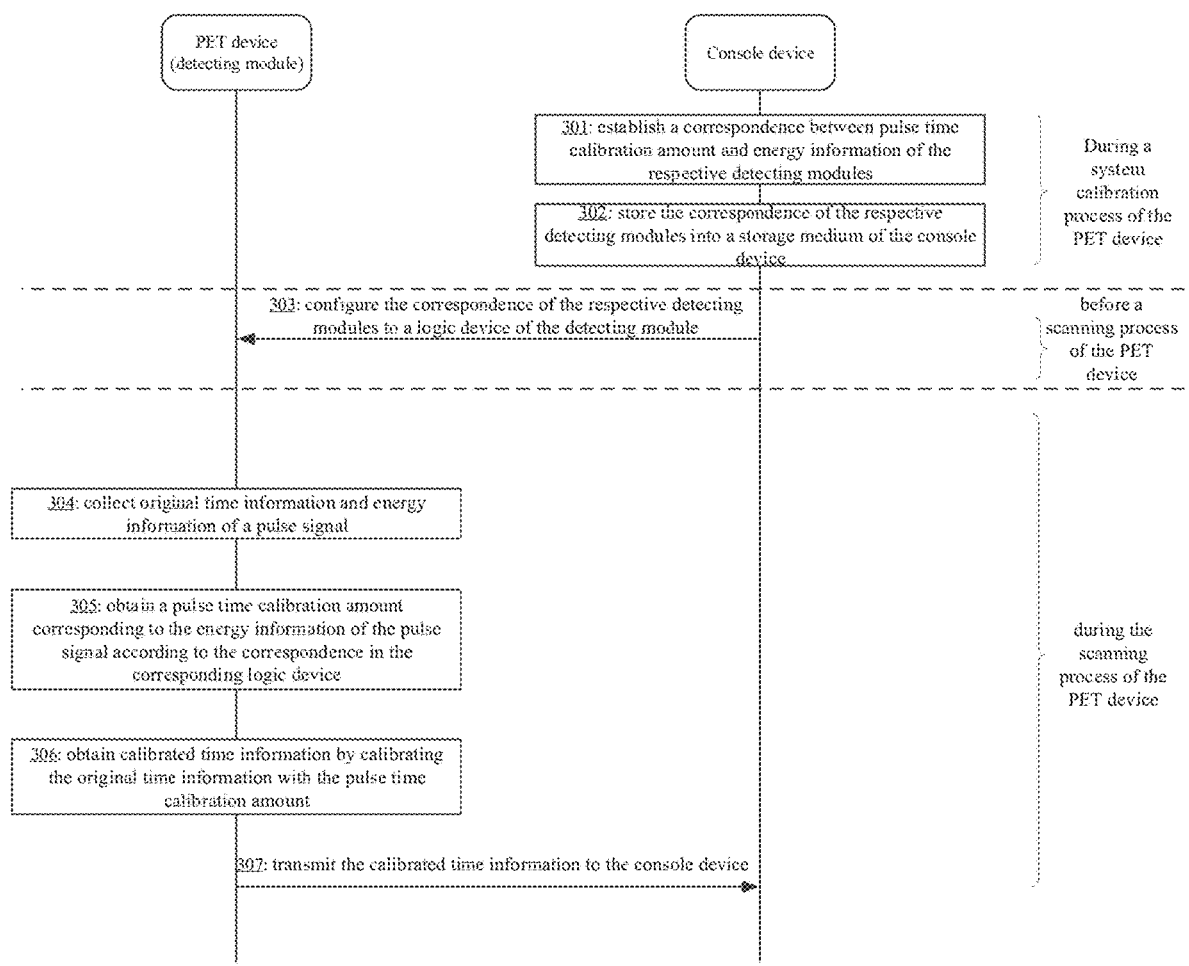
FIG. 3 is a flow chart of a method of calibrating time in a PET device.

FIG. 3 is a flow chart of an example method of calibrating time in the PET device. This example illustrates a process of calibrating time which is finished on the PET device through interaction between the PET device and the console device. The process may include elements 301-307.

The console device establishes a correspondence between pulse time calibration amount and energy information of the detecting modules during a system calibration process of the PET device (301). The console device stores the correspondence between pulse time calibration amount and energy information of the detecting modules in a storage medium of the console device or in a remote storage medium (302). The console device configures the correspondence of the detecting modules to a logic device of the detecting module before a scanning process of the PET device (303).

The detecting module collects original time information and energy information of a pulse signal during the scanning process of the PET device (304). The detecting module obtains a pulse time calibration amount corresponding to the energy information of the pulse signal according to the correspondence in the logic device (305). The detecting module obtains calibrated time information by calibrating the original time information with the pulse time calibration amount (306). The detecting module transmits the calibrated time information to the console device (307).

Figure 4:
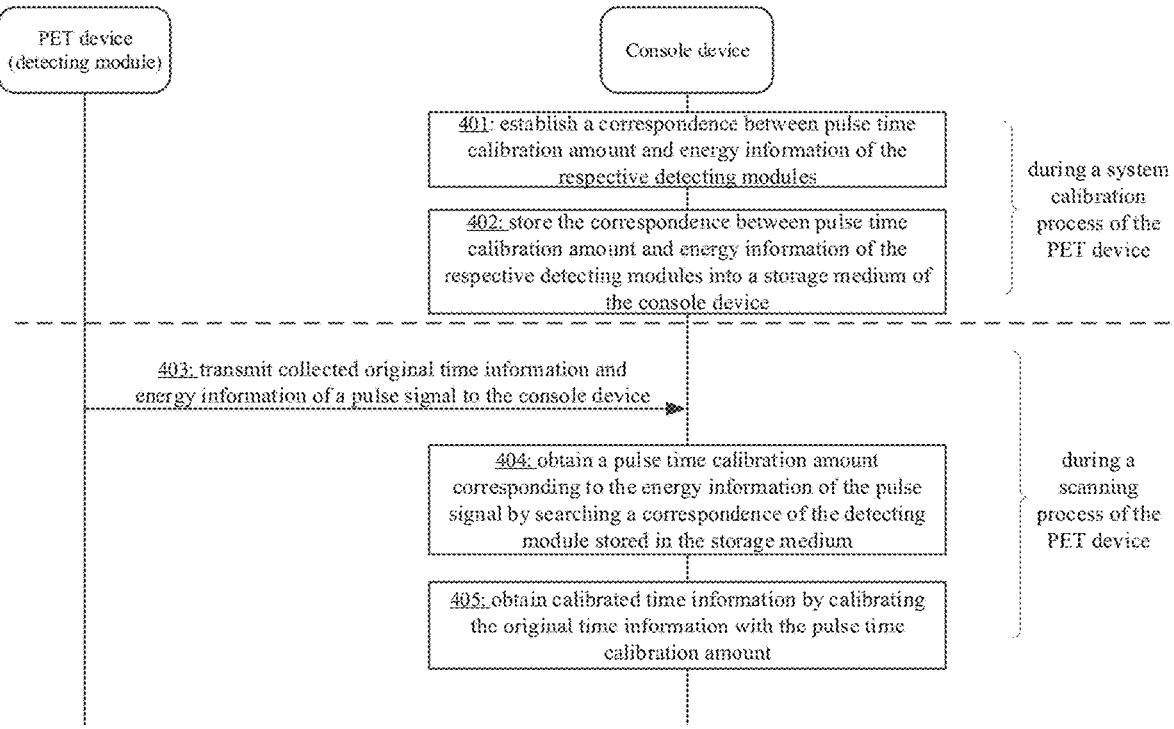
FIG. 4 is a flow chart of a method of calibrating time in a PET device.

FIG. 4 is a flow chart of an example method of calibrating time in the PET device. This example illustrates a process of calibrating time which is finished on the console device through interaction between the PET device and the console device. The process may include elements 401-405.

The console device establishes a correspondence between pulse time calibration amount and energy information of the detecting modules during a system calibration process of the PET device (401). The console device stores the correspondence between pulse time calibration amount and energy information of the detecting modules in a storage medium of the console device or in a remote storage medium (402).

The console device receives original time information and energy information of a pulse signal collected by the detecting module during the scanning process of the PET device (403). The console device obtains a pulse time calibration amount corresponding to the energy information of the pulse signal by searching a correspondence of the detecting module stored in the storage medium (404). The console device obtains calibrated time information by calibrating the original time information with the pulse time calibration amount to reconstruct a PET image (405).

The processes depicted in FIG. 3 and FIG. 4 are described with respect to FIG. 2A.

The order of execution of the respective steps in the above-described flowcharts shown in FIGS. 2A, 3 and 4 are not limited to the order in the respective flowcharts. In addition, the description of the respective steps may be implemented in the form of software, hardware, or a combination thereof. For example, those skilled in the art may implement it as a software code, including machine executable instructions to enable logical function corresponding to the respective steps. When it is implemented in the form of software, the machine executable may be stored in a memory and executed by a processor in the device.

Figure 5:
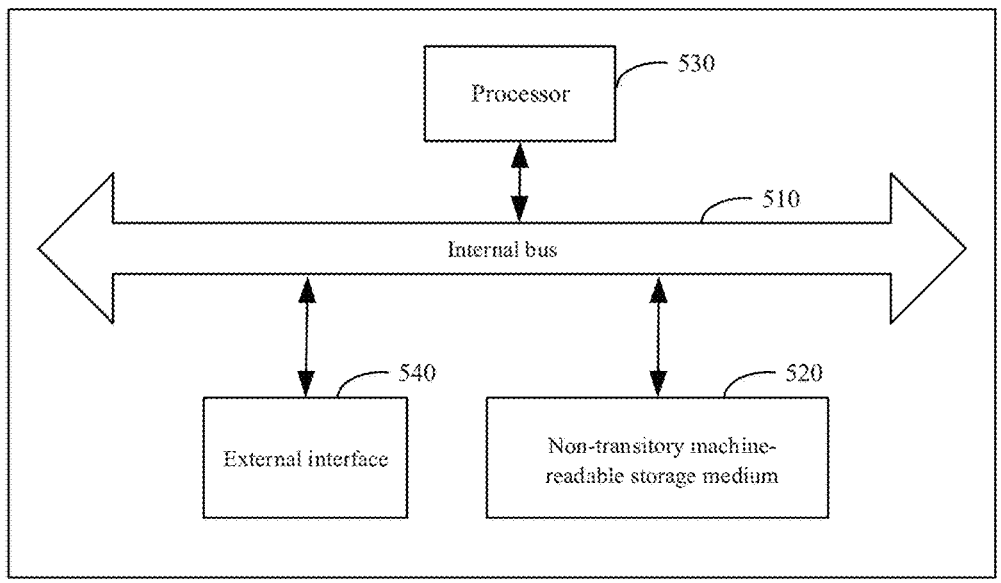
FIG. 5 is a schematic diagram of a hardware structure of a PET system.

FIG. 5 is a schematic diagram of an example hardware structure of a PET system. The PET system includes an internal bus 510, a non-transitory machine-readable storage medium 520, a processor 530, an external interface 540, and a PET device (not shown in FIG. 5) coupled to the external interface 540. The processor 530 may read the machine executable instructions stored in the non-transitory machine-readable storage medium 520 to perform the method of calibrating time described above.

In some examples, by invoking machine executable instructions stored in the non-transitory machine readable storage medium, the processor is caused to: obtain original time information and energy information of a first pulse signal collected by a detecting module during a scanning process of the PET device, wherein a detector of the PET device comprises a plurality of detecting modules, and the original time information of the first pulse signal comprises a moment at which an amplitude of the first pulse signal begins to be greater than a threshold; determine a pulse time calibration amount corresponding to the energy information of the first pulse signal according to stored information indicative of a correspondence between the pulse time calibration amount and the energy information of each detecting module; generate calibrated time information by calibrating the original time information with the pulse time calibration amount; and reconstruct a PET image based on the generated calibrated time information.

In an example, the processor is further caused to: establish a correspondence between the pulse time calibration amount and the energy information of each of the detecting modules during a system calibration process of the PET device; and store the correspondence between the pulse time calibration amount and the energy information of each of the detecting modules.

The correspondence between the pulse time calibration amount and the energy information of a given detecting module is characterized by any one of following function relationships: a linear function, an exponential function, a power function and polynomial function. Each of the function relationships comprises a function model and function parameters corresponding to the function model. The correspondence between pulse time calibration amount and energy information of the respective detecting modules in the detector is characterized by a same function model.

In an example, when establishing the correspondence between the pulse time calibration amount and the energy information of a given detecting module, the processor is caused to: determine a function model; obtain data of second pulse signals collected by the detecting module during the system calibration process; and determine values of one or more function parameters corresponding to the function model by calculating the data of the second pulse signals. The data of the second pulse signals is calculated by a fitting algorithm or an iterative algorithm.

In an example, when obtaining the data of the second pulse signals collected by the detecting module during the system calibration process, the processor is caused to: obtain information of N second pulse signals, e.g., a preset number N of second pulse signals, by sampling output of the detecting module during the system calibration process with a sampling module, wherein, N is an integer greater than 1, the information of each of the N second pulse signals comprises a combination of amplitude information and time information, and the sampling module comprises a data acquisition card or an oscilloscope; obtain energy information of each of the N second pulse signals by performing a numerical integration operation for the amplitude information of the second pulse signal; and obtain a pulse time calibration amount of each of the N second pulse signals by calculating a difference between a start moment and an over-threshold moment of the second pulse signal, wherein the over-threshold moment of the second pulse signal indicates a moment at which an amplitude of the second pulse signal begins to be greater than the threshold.

In an example, when calculating the data of the second pulse signals by the iterative algorithm, the processor is caused to: take the one or more function parameters corresponding to the function model as iteration variables; determine new time information of each of the second pulse signals based on a value of the respective function parameters, energy information of the second pulse signal and time information of the second pulse signal obtained in a prior iteration; and when a system time resolution obtained based on the new time information of each of the second pulse signals reaches an optimum, take values of the iteration variables corresponding to the optimum as the values of the one or more function parameters when the function model is applied to the detecting module.

In an example, when storing the correspondence between the pulse time calibration amount and the energy information of the respective detecting modules, the processor is caused to perform one of: storing a function model and one or more function parameters corresponding to the function model; and storing a pulse time calibration amount-energy information table for each of the detecting modules, wherein energy information and a pulse time calibration amount generated by the correspondence are recorded in an entry of the table.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description provides examples and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications fall within the protection scope of the technical scheme of the present disclosure. Accordingly, other embodiments are within the scope of the following claims.

What is claimed is:

1. A method of calibrating time in a Positron Emission Tomography (PET) device, comprising:
   obtaining original time information and energy information of a first pulse signal collected by a detecting module during a scanning process of the PET device, wherein a detector of the PET device comprises a plurality of detecting modules, and the original time information of the first pulse signal comprises a moment at which an amplitude of the first pulse signal begins to be greater than a threshold;
   determining a pulse time calibration amount corresponding to the energy information of the first pulse signal according to stored information indicative of a correspondence between the pulse time calibration amount and the energy information of each detecting module;
   generating calibrated time information of the first pulse signal by calibrating the original time information with the pulse time calibration amount; and
   reconstructing a PET image based on the generated calibrated time information.

2. The method of claim 1, comprising:
   establishing a correspondence between the pulse time calibration amount and the energy information of each of the detecting modules during a system calibration process of the PET device; and
   storing the correspondence between the pulse time calibration amount and the energy information of each of the detecting modules.

3. The method of claim 2, wherein the correspondence between the pulse time calibration amount and the energy information of a given detecting module is characterized by any one of following function relationships: a linear function, an exponential function, a power function and a polynomial function;
   wherein each of the function relationships comprises a function model and function parameters corresponding to the function model.

4. The method of claim 3, wherein the correspondence between the pulse time calibration amount and the energy information of each of the detecting modules in the detector is characterized by the same function model.

5. The method of claim 3, wherein establishing the correspondence between the pulse time calibration amount and the energy information of a given detecting module comprises:
   determining a function model;
   obtaining data of second pulse signals collected by the detecting module during the system calibration process; and
   determining values of one or more function parameters corresponding to the function model by calculating the data of the second pulse signals.

6. The method of claim 5, wherein obtaining the data of the second pulse signals collected by the detecting module during the system calibration process comprises:
   obtaining information of N second pulse signals by sampling output of the detecting module during the system calibration process with a sampling module, wherein N is an integer greater than 1, and wherein the information of each of the N second pulse signals comprises a combination of amplitude information and time information, and the sampling module comprises a data acquisition card or an oscilloscope;
   obtaining energy information of each of the N second pulse signals by performing a numerical integration operation for the amplitude information of the second pulse signal; and
   obtaining a pulse time calibration amount of each of the N second pulse signals by calculating a difference between a start moment and an over-threshold moment of the second pulse signal, wherein the over-threshold moment of the second pulse signal indicates a moment at which an amplitude of the second pulse signal begins to be greater than the threshold.

7. The method of claim 5, wherein calculating the data of the second pulse signals comprises:
   calculating the data of the second pulse signals by a fitting algorithm.

8. The method of claim 5, wherein calculating the data of the second pulse signals comprises:
   calculating the data of the second pulse signals by an iterative algorithm.

9. The method of claim 8, wherein calculating the data of the second pulse signals by the iterative algorithm comprises:
   taking the one or more function parameters corresponding to the function model as iteration variables;
   determining new time information of each of the second pulse signals based on a value of the respective function parameters, energy information of the second pulse signal and time information of the second pulse signal obtained in a prior iteration; and
   when a system time resolution obtained based on the new time information of each of the second pulse signals reaches an optimum, taking values of the iteration variables corresponding to the optimum as the values of the one or more function parameters when the function model is applied to the detecting module.

10. The method of claim 2, wherein storing the correspondence between the pulse time calibration amount and the energy information of the respective detecting modules comprises one of:
    storing a function model and one or more function parameters corresponding to the function model; and
    storing a pulse time calibration amount-energy information table for each of the detecting modules, wherein record energy information and a pulse time calibration amount generated by the correspondence are recorded in an entry of the table.

11. A PET system, comprising:
    a PET device;
    one or more processors; and
    a non-transitory machine readable storage medium;
    wherein the one or more processors are configured to invoke machine executable instructions stored in the non-transitory machine readable storage medium to:
       obtain original time information and energy information of a first pulse signal collected by a detecting module during a scanning process of the PET device, wherein a detector of the PET device comprises a plurality of detecting modules, and the original time information of the first pulse signal comprises a moment at which an amplitude of the first pulse signal begins to be greater than a threshold;

determine a pulse time calibration amount corresponding to the energy information of the first pulse signal according to stored information indicative of a correspondence between the pulse time calibration amount and the energy information of each detecting module;

generate calibrated time information of the first pulse signal by calibrating the original time information with the pulse time calibration amount; and reconstruct a PET image based on the generated calibrated time information.

12. The system of claim 11, wherein the one or more processors are configured to invoke the machine executable instructions to:

establish a correspondence between the pulse time calibration amount and the energy information of each of the detecting modules during a system calibration process of the PET device; and store the correspondence between the pulse time calibration amount and the energy information of each of the detecting modules.

13. The system of claim 12, wherein the correspondence between the pulse time calibration amount and the energy information of a given detecting module is characterized by any one of following function relationships: a linear function, an exponential function, a power function and a polynomial function;

wherein each of the function relationships comprises a function model and function parameters corresponding to the function model.

14. The system of claim 13, wherein the correspondence between the pulse time calibration amount and the energy information of each of the detecting modules in the detector is characterized by the same function model.

15. The system of claim 13, wherein establishing the correspondence between the pulse time calibration amount and the energy information of a given detecting module comprises:

determining a function model;

obtaining data of second pulse signals collected by the detecting module during the system calibration process; and determining values of one or more function parameters corresponding to the function model by calculating the data of the second pulse signals.

16. The system of claim 15, wherein obtaining the data of the second pulse signals collected by the detecting module during the system calibration process comprises:

obtaining information of N second pulse signals by sampling output of the detecting module during the system calibration process with a sampling module, wherein, N is an integer greater than 1, the information of each of the N second pulse signals comprises a combination of amplitude information and time information, and the sampling module comprises a data acquisition card or an oscilloscope;

obtaining energy information of each of the N second pulse signals by performing a numerical integration operation for the amplitude information of the second pulse signal; and obtaining a pulse time calibration amount of each of the N second pulse signals by calculating a difference between a start moment and an over-threshold moment of the second pulse signal, wherein the over-threshold moment of the second pulse signal indicates a moment at which an amplitude of the second pulse signal begins to be greater than the threshold.

17. The system of claim 15, wherein calculating the data of the second pulse signals comprises:

calculating the data of the second pulse signals by a fitting algorithm.

18. The system of claim 15, wherein calculating the data of the second pulse signals comprises:

calculating the data of the second pulse signals by an iterative algorithm.

19. The system of claim 18, wherein calculating the data of the second pulse signals by the iterative algorithm comprises:

take the one or more function parameters corresponding to the function model as iteration variables;

determine new time information of each of the second pulse signals based on a value of the respective function parameters, energy information of the second pulse signal and time information of the second pulse signal obtained in a prior iteration; and when a system time resolution obtained based on the new time information of each of the second pulse signals reaches an optimum, take values of the iteration variables corresponding to the optimum as the values of the one or more function parameters when the function model is applied to the detecting module.

20. The system of claim 12, wherein storing the correspondence between pulse time calibration amount and energy information of the respective detecting modules comprises:

storing a function model and one or more function parameters corresponding to the function model; and storing a pulse time calibration amount-energy information table for each of the detecting modules, wherein energy information and a pulse time calibration amount generated by the correspondence are recorded in an entry of the table.

* * * * *